United States Patent [19]
Hoekstra et al.

[11] Patent Number: 6,156,732
[45] Date of Patent: Dec. 5, 2000

[54] AZOLE PEPTIDOMIMETICS AS THROMBIN RECEPTOR ANTAGONISTS

[75] Inventors: William Hoekstra, Villanova; Becky L. Hulshizer, North Wales, both of Pa.

[73] Assignee: Ortho-McNeil Pharmaceuticals, Inc., Raritan, N.J.

[21] Appl. No.: 09/387,489

[22] Filed: Sep. 1, 1999

Related U.S. Application Data

[62] Division of application No. 09/245,739, Feb. 8, 1999, Pat. No. 6,017,890
[60] Provisional application No. 60/075,171, Feb. 19, 1998.
[51] Int. Cl.$^7$ .......................... A61K 38/03; A61K 38/04; A61K 38/07; A61K 38/08
[52] U.S. Cl. .................................. 514/18; 514/2; 514/17; 514/822
[58] Field of Search .................................. 514/2, 17, 18, 514/822

[56] References Cited

FOREIGN PATENT DOCUMENTS

WO 89/1141A  11/1989  WIPO.
WO 89/11492A  11/1989  WIPO.

OTHER PUBLICATIONS

Ervin, P.R. et al, (1995) *Proceedings of the American Association for Cancer Research, Annual Meeting*, 36:627, Abstract #3731, "The Active Species of Mammastatin as Expressed in Normal Mammary Cells but not in Mammary Carcinomas".
Ervin, P.R., (Mar. 1996) *Proceedings of the American Association for Cancer Research Annual Meeting*, 37:399, Abstract #2722, "Expression and Testing of Recombinant Mammastatin".
Ervin, P.R. et al., (1993) *Proceeding of the American Association for Cancer Research, Annual Meeting*, 34:150, Abstract #893, "Phosphoralation of the Growth Inhibitor Mammastatin in Normal but not Transformed Human Mammary Cells".
Ervin, P.R. et al., (Jun. 30, 1989) *Science*, 244:1585–1587 "Production of Mammastatin, a Tissue Specific Growth Inhibitor by Normal Human Mammary Cells".
Ervin, P.R., (1995) PHD Thesis from the University of Michigan, pp. 1–131 "Further Characterization and Cloning of the Growth Inhibitor Mammastatin".
Freemont et al., (Jan. 1984) *Archives of Biochemistry and Biophysics*, 228(1):342–352 "Human Skeletal—Muscle Aldolase: N–Terminal Sequence Analysis of CNBr—and o—Iodosobenzoic Acid—Cleavage Fragments".
Garner I., (1994) *Methods of Molecular Biology*, 28:41–47 "Isolation of Total and Poly A+ RNA from Animal Cells".
Jerala, (1992) *Biotechniques*, 13:564 "Simultaneous Synthesis of Degenerate Oligo—nucleotides of Variable Length".
Kroczek, R.A., (1993) *Journal of Chromatography*, 618:133–145 "Review: Southern and Northern analysis".
Lasken, R.S. et al., (1985) *Proceedings of the National Academy of Science U.S.A.*, 82(5):1301–1305 "A fidelity assay using "dideoxy" DNA sequencing: A measurement of sequence dependence and frequency of forming 5–bromouracil guanine base mispairs".
Nakayama, K. et al., (Jun. 1988) *Bio/Technology*, 6:693–697 "Construction of an ASD+ Expression—Cloning Vector: Stable Maintenance and High Level Expression of Cloned Genes in a Salmonella Vaccine Strain".
Nguyen, B. et al., (1995) *Critical Reviews and Oncology/Hematology*, 20:223–236 "The Biology of Growth Regulation in Normal and Malignant Breast Epithelium: From Bench to Clinic".
Short, J.M. et al., (Aug. 11, 1988) *Nucleic Acids Research*, 16(15):7583–7601 "λ ZAP: a bacteriophage λ expression vector with in vivo excision properties".
Soule, et al., (Jan. 1986) *In Vitro Cellular & Developmental Biology*, 22(1):6–12 "A Simplified Method For Passage and Long—Term Growth of Human Mammary Epithelial Cells".
Stuckey, J.A. et al., (Aug. 18, 1994) *Nature*, 370:571–575 "Crystal structure of Yersinia protein tyrosine phosphatase at 2.5 Å and the complex with tungstate".
Towbin H. et al., (1989) *Journal of Clinical Chemistry, Clinical Biochemistry*, 27(8):495–501 "Immumoblotting in the Clinical Laboratory".
Ullah et al., (Aug. 30, 1994) *Biocheical and Biophysical Research Communications*, 203(1):182–189 "The Complete Primary Structure Elucidation of *Aspergillus ficuum* (NIGER), pH 6.0, Optimum Acid Phosphatase".

*Primary Examiner*—Bennett Celsa
*Attorney, Agent, or Firm*—Ralph R. Palo

[57] ABSTRACT

Azole derivatives of formula (I):

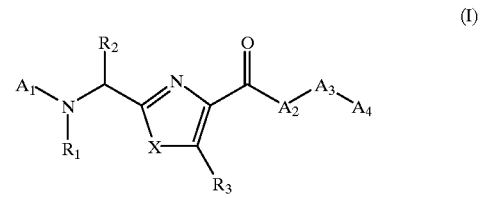

are disclosed as useful in treating platelet-mediated thrombotic disorders.

2 Claims, No Drawings

SEQUENCE LISTING

<160> NUMBER OF SEQ ID NOS: 2

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence:synthetic

<400> SEQUENCE: 1

Ser Phe Leu Leu Arg Asn
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence:synthetic

<400> SEQUENCE: 2

Ser Phe Arg Leu Arg Lys Tyr
1               5

AZOLE PEPTIDOMIMETICS AS THROMBIN RECEPTOR ANTAGONISTS

This is a provision of Ser. No. 60/075,171 filed Feb. 14, 1998 and a division of application Ser. No. 09/245,739, filed Feb. 8, 1999 and now U.S. Pat. No. 6,017,890.

BACKGROUND OF THE INVENTION

Thrombin is an important serine protease in hemostatis and thrombosis. One of the key actions of thrombin is receptor activation. A functional human thrombin receptor, cloned by Coughlin in 1991 (T.-K. Vu, *Cell* 1991, 64, 1057), was found to be a member of the G-protein coupled receptor (GPCR) superfamily. The receptor activation putatively occurs by N-terminal recognition and proteolytic cleavage at the Arg-41/Ser-42 peptide bond to reveal a truncated N-terminus. This new receptor sequence, which has an SFLLRN [SEQ ID.:1] (Ser-Phe-Leu-Leu-Arg-Asn) N-terminus acting as a tethered ligand to recognize a site on the receptor, can trigger activation and signal transduction leading to platelet aggregation. Since 1991, two other protease-activated receptors with extensive homology to the thrombin receptor, "PAR-2" (S. Nystedt, *Proc. Natl. Acac. Sci USA* 1994, 91, 9208) and "PAR-3" (H. Ishihara, *Nature* 1997, 386, 502), were cloned, and found to be activated by similar N-terminal hexapeptide sequences. Thrombin receptor (PAR-1) specific antibody-induced blockade of the platelet thrombin receptor has shown efficacy against arterial thrombosis in vivo (J. J. Cook *Circulation* 1995, 91, 2961). Hence, antagonists of the thrombin receptor based on SFLLRN are useful in antagonizing these protease-activated receptors and as such may be used to treat platelet mediated thrombotic disorders such as myocardial infarction, stroke, restenosis, angina, atherosclerosis, and ischemic attacks by virtue of their ability to prevent platelet aggregation.

The thrombin receptor has also been identified on other cell types: endothelial, fibroblast, osteosarcoma, smooth muscle, and neuronal/glia. Thrombin activation of endothelial cells upregulates P-selectin to induce polymorphonuclear leukocyte adhesion—an inflammatory response of the vessel wall (Y. Sugama, *J. Cell Biol.* 1992, 119, 935). In fibroblasts, thrombin receptor activation induces proliferation and transmission of mitogenic signals (D. T. Hung, *J. Cell Biol.* 1992, 116, 827). Thrombin has been implicated in osteoblast proliferation through its activation of osteoblast cells (D. N. Tatakis, *Biochem. Biophys. Res. Commun.* 1991, 174, 181). Thrombin has been implicated in the regulation and retraction of neurons (K. Jalink, *J. Cell. Biol.* 1992, 118, 411). Therefore, in this context the antogonist compounds of this invention may also be useful against inflammation, restenosis, osteoporosis, and neurodegenerative disorders.

The compounds of the present invention are azole peptidomimetics represented by the general formula (I) below. Azole-containing cyclic peptides have been synthesized to be employed as cytotoxic agents (C. Boden, *Tetrahedron Lett.* 1994, 35, 8271). By contrast, the azole peptidomimetics of the present invention are strictly acyclic with activity against the thrombin receptor. Azole-based dolastatin analogues have been prepared as antitumor agents (K.Sakakibara, PCT Int. Appl., 31 pp., WO9633212). These compounds contain a 4-thiazole-alkylamide C-terminus, whereas the compounds of the present invention require at least two amino acid residues C-terminal to the 4-thiazole carboxamide for activity against the thrombin receptor. Similarly, azole endothelin antagonists have been prepared which contain a 4-thiazole-carboxylic acid C-terminus (T. von Geldern, *J. Med. Chem.* 1996, 39, 957).

DISCLOSURE OF THE INVENTION

The present invention is directed to compounds represented by the following general formula (I):

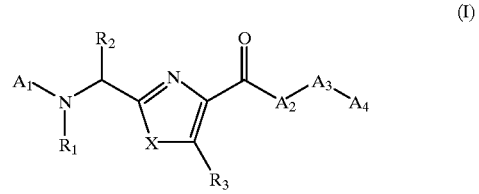

wherein A1, A2, A3, A4, R1, R2, R3, and X are as hereinafter defined. The compounds of the present invention are platelet aggregation inhibitors and as such are useful in treating platelet-mediated thrombotic disorders such as arterial and venous thrombosis, acute myocardial infarction, reocclusion following thrombolytic therapy and angioplasty, inflammation, unstable angina, and a variety of vaso-occlusive disorders. These compounds are also useful as antithrombotics in conjunction with fibrinolytic therapy (e.g., t-PA or streptokinase). Pharmaceutical compositions containing such compounds as the active ingredient as well as methods of preparing the compounds are also part of the present invention.

DETAILED DESCRIPTION OF THE INVENTION

More particularly, the present invention is directed to compounds of the following formula (I):

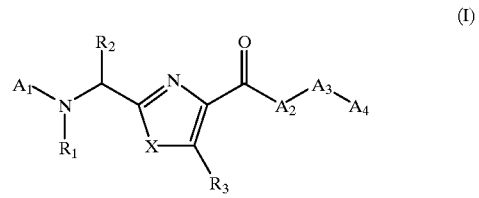

wherein $A_1$ is an amino acid residue selected from Sar, Gly, His, His(CH$_2$Ph), Ile Ser, Thr, β-Ala, or Ala. $A_1$ may also be a $C_2$–$C_6$-acyl group such as, for example, acetyl, propionyl or butyryl or a $C_1$–$C_8$-alkyl group such as, for example, methyl, ethyl, propyl or butyl;

wherein $A_2$ is an alkyl amino acid residue selected from Cha, Leu, Ile, Asp, and Glu or an amino alkyl amino acid residue such as Lys, His, Orn, homoArg and Arg;

wherein $A_3$ is an amino alkyl amino acid residue selected from Lys, His, Orn, Arg and homoArg;

wherein $A_4$ is an arylalkyl residue selected from Phe and Tyr or an aralkylamino group such as benzylamino or a phenethylamino group;

wherein $R_1$ is selected from H or alkyl;

wherein $R_2$ is an aryl, substituted aryl, heteroaryl, substituted heteroaryl, aralkyl or substituted aralkyl group, however $R_2$ is preferably aralkyl;

wherein $R_3$ is selected from H or alkyl;

wherein X is selected from S, O, or $NR_4$, wherein $R_4$ is selected from H or alkyl;

and the pharmaceutically acceptable salts thereof.

As used herein, unless otherwise noted alkyl and alkoxy whether used alone or as part of a substituent group, include straight and branched chains having 1–8 carbons. For example, alkyl radicals include methyl, ethyl, propyl, isopropyl, n-butyl, isobutyl, sec-butyl, t-butyl, n-pentyl, 3-(2-methyl)butyl, 2-pentyl, 2-methylbutyl, neopentyl, n-hexyl, 2-hexyl, 2-methylpentyl and the like. Alkoxy radicals are oxygen ethers formed from the previously described straight or branched chain alkyl groups. Acyl radicals are residues having 2–6 carbon atoms derived from an organic acid by removal of the hydroxyl group.

The terms "aryl", "heteroaryl", "substituted aryl" and "substituted heteroaryl" as used herein alone or in combination with other terms indicates aromatic or heteroaromatic groups such as phenyl, naphthyl, pyridyl, thienyl, furanyl, or quinolinyl wherein the substituent is a halo, alkyl, amino, nitro or alkoxy group. The term "aralkyl" means an alkyl group substituted with an aryl group.

Unless otherwise indicated, the other substituent on the carbon to which $R_2$ is attached to hydrogen.

The compounds of the present invention may also be present in the form of a pharmaceutically acceptable salt. The pharmaceutically acceptable salt generally takes a form in which the basic nitrogen is protonated with an inorganic or organic acid. Representative organic or inorganic acids include hydrochloric, hydrobromic, hydriodic, perchloric, sulfuric nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic.

Particularly preferred compounds of the present invention include those compounds shown in Table I, where the amino acids bear the "L" absolute configuration unless denoted otherwise.

TABLE I

| # | R3 | A1 | A2 | A3 | A4 | X |
|---|----|----|----|----|----|----|
| 1 | H | Sar | Cha | Arg | $NHCH_2Ph$ | O |

TABLE I-continued

| # | R3 | A1 | A2 | A3 | A4 | X |
|---|----|----|----|----|----|----|
| 2 | H | β-Ala | Cha | Arg | $NHCH_2Ph$ | O |
| 3 | H | Sar | Cha | Arg | $NH(CH_2)_2Ph$ | S |
| 4 | H | Sar | Cha | hArg | $Phe-NH_2$ | S |
| 5 | H | Ile | Cha | Arg | $Phe-NH_2$ | S |
| 6 | H | Sar | Lys | Arg | $NH(CH_2)_2Ph$ | S |
| 7 | Me | Sar | Cha | Arg | $NHCH_2Ph$ | O |
| 8 | Me | $His(CH_2Ph)$ | Cha | Arg | $NHCH_2Ph$ | O |
| 9 | Me | Ac | Cha | Arg | $NHCH_2Ph$ | O |
| 10 | Me | $Me_2$ | Cha | Arg | $NHCH_2Ph$ | O |

The antagonists of the present invention may be prepared as shown in Scheme AA. Protected oxazole intermediates (AA2) can be prepared in two steps from the corresponding dipeptide (AA1) by Burgess Reagent-mediated cyclization to the oxazoline and then oxidation with, for example, t-butyl peroxybenzoate to give the oxazole (AA2). Dipeptides such as AA1 can be synthesized from the corresponding protected amino acids using standard solution-phase peptide coupling conditions utilizing EDC as the activating agent, NMM as the base and DCM as the solvent. Standard peptide methods are employed to complete the synthesis (e.g. compound 1). Boc removal from AA2 utilizing an acid such as, for example, TFA or HCl and coupling with Boc-Sar-OSu affords AA3. The ester is then saponified with a base such as, for example, lithium hydroxide or any alkali metal or alkaline earth metal base and the carboxylic acid product is coupled with H-Cha-OMe to give AA4. Saponification of AA4 wit a base, such as lithium hydroxide, for example, coupling with H-Arg(Pmc)-NHBn (EDC), and deprotection with TFA affords the product (1). The aforementioned Arg reagent, and other Arg amides in general, can be prepared in two steps from Fmoc-Arg(Pmc)-OH by EDC-mediated coupling with benzylamine and then Fmoc removal with 20% piperidine in dioxane. Although the Scheme is used to illustrate the preparation of those compounds wherein $R_2$ is p-F-Ph, all of the compounds of the present invention can be prepared using the method illustrating in Scheme AA by utilizing an appropriately substituted oxazole, thiazole or imidazole as the starting material. Intermediate azoles other than oxazole AA2 can be prepared according to the methods exemplified in Schemes AB, AC, and AD.

SCHEME AA

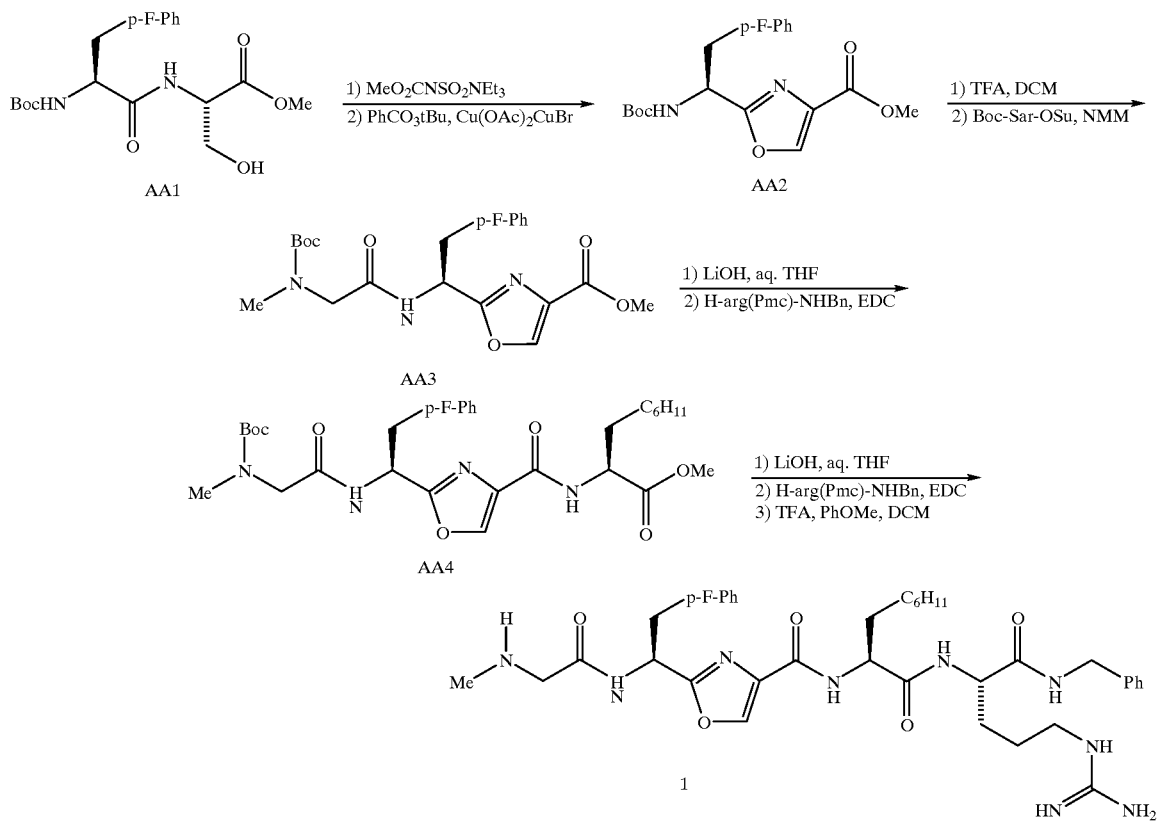

SCHEME AB

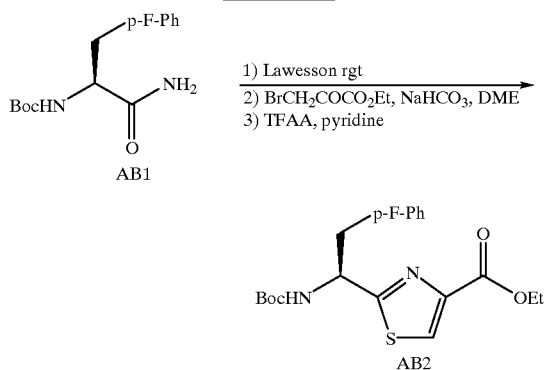

The thiazole intermediate AB2 can be prepared in three steps from an amino acid residue (AB1) using Hantzsch cyclization methodology (Scheme AB). AB1 is converted to the corresponding thioamide using Lawesson's Reagent. The thioamide is then alkylated with ethyl 3-bromopyruvate, and the product is cyclized with trifluoroacetic anhydride to give AB2. Those compounds of the present invention wherein X is S can be prepared from AB2 using standard peptide coupling procedures as exemplified in Scheme AA.

SCHEME AC

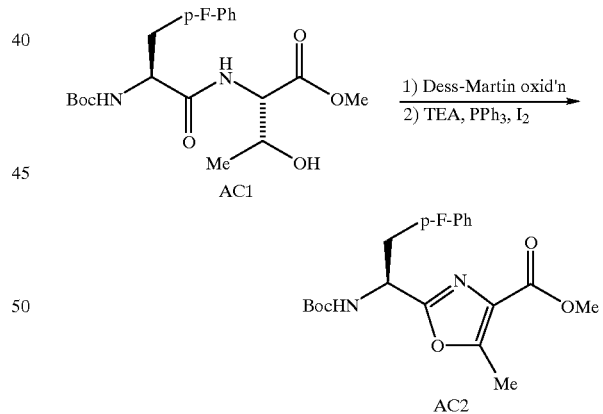

The 5-methyl-oxazole intermediate AC2 can be prepared in two steps from a dipeptide (AC1) (Scheme AC). AC1 is converted to the corresponding methyl ketone using the Dess-Martin reagent and the methyl ketone is then cyclized with triphenylphosphine/iodine to give AC2. In the case of compound 10, the N,N-dimethyl-p-F-Phe derivative is prepared by reductive alkylation with, for example, formaldehyde/sodium triacetoxyborohydride following Boc removal with, for example, TFA from AC2, and then the synthesis completed as shown in Scheme AA.

Those starting materials wherein X is $NR_4$ can be synthesized according to methods known to those skilled in the art. (S. K. Thompson, *J. Med. Chem.* 1994, 37, 3100). In this procedure, EDC-mediated coupling of Boc-p-Phe-OH (AD1) with 4-amino-isoxazole followed by hydrogenation ($H_2$/Pd-C) and sodium hydroxide-mediated cyclization provides the corresponding 2-substituted-imidazole-4-carboxaldehyde (AD2, Scheme AD). Oxidation of this aldehyde to the corresponding imidazole-4-carboxylic acid using standard methods ($NAClO_2$) and trimethylsilyldiazomethane esterification provides the imidazole AD3. Those compounds of the present invention wherein X is $NR_4$ can be prepared from AD3 using standard peptide coupling procedures as exemplified in Scheme AA. Alkylation of the imidazole by generally known techniques produces those compounds of the invention wherein $R_4$ is alkyl.

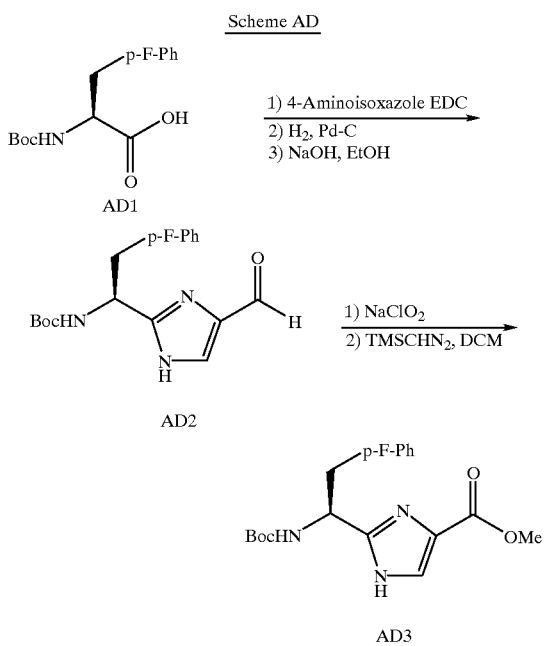

Scheme AD

To prepare the pharmaceutical compositions of this invention, one or more compounds of formula (I) or salt thereof of the invention as the active ingredient, is intimately admixed with a pharmaceutical carrier according to conventional pharmaceutical compounding techniques, which carrier may take a wide variety of forms depending on the form of preparation desired for administration, e.g., oral or parenteral such as intramuscular. In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.03 mg to 100 mg/kg (preferred 0.1–30 mg/kg) and may be given at a dosage of from about 0.1–300 mg/kg/day (preferred 1–50 mg/kg/day). The dosages, however, may be varied depending upon the requirement of the patients, the severity of the condition being treated and the compound being employed. The use of either daily administration or post-periodic dosing may be employed.

BIOLOGY

The compounds of the present invention interrupt platelet activation induced by thrombin's proteolytic cleavage of its platelet surface receptor, and thereby inhibit platelet aggregation. Such compounds are, therefore, useful in treating platelet-mediated thrombotic disorders such as arterial and venous thrombosis, acute myocardial infarction, reocclusion following thrombolytic therapy and angioplasty, and a variety of vaso-occlusive disorders.

IN VITRO THROMBIN RECEPTOR BINDING ASSAY

CHRF membranes (Jones, *Biochim. Biophys. Acta* 1992, 1136, 272) are thawed from −70° C., centrifuged at maximum speed for 5 min, washed twice with binding buffer (50 mM HEPES containing 5 mM $MgCl_2$ and 0.1% BSA), and re-suspended in binding buffer (25 μg/100 mL). 100 μl of membranes are added to the 24-Wallac plates and delivered to the Tomtech apparatus. In a typical experiment, 6 μl of samples (from a 125 μg/mL intermediary plate, 20%DMSO) and 44 μl buffer are delivered to the plates (final conc. of compounds is 3.7 μg/mL, 0.6% DMSO). Similarly, 6 μl 20%DMSO and 44 μl buffer are delivered to both column 1 (NSB) and column 12 (TB). 10 μl Ser-pFPhe-Har-Leu-Har-Lys-Tyr-$NH_2$ [SEQ ID.:2] (721-40; 500 μM in deionized water) is added to column 1. 50 μl tritiated 721-40 (specific activity 46 Ci/mmol) is added to all the wells. The plates are mixed well for 20 seconds, incubated for 30 min, and then harvested with 10 mM HEPES/138 mM NaCl using the Skatron harvester. The filters (GF/C Brandel FPXLR 296) are presoaked 3 h in 0.5% polyethyleneimine in HEPES/0.1 M N-acetylglucosamine) are set in saran wrap and dried for 3 min in the microwave, and placed in sample bags (Wallac 1450-432). 4.5 mL scintillation fluid (Wallac, Betaplate Scint 1205-440) is added. The bags are sealed, placed in filter cassettes (Wallac 1450-104), and analyzed on the microbeta counter.

IN VITRO INHIBITION OF THROMBIN-INDUCED GEL-FILTERED PLATELET AGGREGATION ASSAY

The percentage of platelet aggregation is calculated as an increase in light transmission of compound-treated platelet concentrate vs. control-treated platelet concentrate. Human blood is obtained from drug free, normal donors in tubes containing 0.13 M sodium citrate. Platelet rich plasma (PRP) is collected by centrifugation of whole blood at 200×g for 10 min at 25° C. The PRP (5 mL) is gel filtered through Sepharose 2B (bed volume 50 mL), and the platelet count is adjusted to 2×10$^7$ platelets per sample. The following constituents are added to a siliconized cuvette: concentrated platelet filtrate and Tyrode's buffer (0.14 M NaCl, 0.0027 M KCl, 0.012 M NaHCO$_3$, 0.76 mM Na$_2$HPO4, 0.0055 M glucose, 2 mg/mL BSA and 5.0 mM HEPES @ pH 7.4) in an amount equal to 350 μl, 50 μl of 20 mM calcium and 50 μl of the test compound. Aggregation is monitored in a BIODATA aggregometer for the 3 min following the addition of agonist (thrombin 50 μl of 1 unit/mL).

Table II shows the biological activity of the compounds of the present invention. The table contains IC$_{50}$ values (μM) of the compounds in a thrombin receptor binding assay, and IC$_{50}$ values (μM) against platelet aggregation stimulated by two agonists, thrombin or SFLLRN-NH$_2$ [SEQ ID.:1] (TRAP).

TABLE II

Biological Activity

| Compound | Thr Receptor Binding IC$_{50}$* | Platelet Aggregation** IC$_{50}$ Thr* | IC$_{50}$ TRAP* |
|---|---|---|---|
| 1 | 2.0 | 25 | 10 |
| 2 | 8.2 | 10 | 7 |
| 3 | 35.0 | 12 | 0.6 |
| 4 | 5.0 | 45 | 3 |
| 5 | 3.5 | 43 | 9 |
| 6 | 15.5 | 26 | 4 |
| 7 | 7.0 | 19 | 22 |
| 8 | 30.0 | 13 | 5 |
| 9 | 31.0 | 24 | 11 |
| 10 | NT | 11 | 17 |

*μM
**Thrombin-induced aggregation of gel-filtered platelets in μM.

EXAMPLES

Protected amino acids were purchased from Fluka Chemical or Bachem Bioscience Inc. All other chemicals were purchased from Aldrich Chemical Company, Inc. High field $^1$H NMR spectra were recorded on a Bruker AC-360 spectrometer at 360 MHz, and coupling constants are given in Herz. Melting points were determined on a Mel-Temp II melting point apparatus and are uncorrected. Microanalyses were performed at Robertson Microlit Laboratories, Inc., Madison, N.J.

In the examples and throughout this application, the following abbreviations have the meanings recited hereinafter:

| Ac | Acetyl |
|---|---|
| Bn | Benzyl |
| Boc | t-Butoxycarbonyl |
| Cbz | Benzyloxycarbonyl |
| CP | compound |
| DCE | 1,2-Dichloroethane |

-continued

| DCM | Dichloromethane |
|---|---|
| DIC | Diisopropylcarbodiimide |
| DIEA | Diisopropylethylamine |
| DMAP | 4-Dimethylaminopyridine |
| DME | 1,2-Dimethoxyethane |
| DMF | N,N-Dimethylformamide |
| EDC | Ethyl dimethylaminopropylcarbodiimide |
| EDTA | Ethylenediaminetetraacetic acid |
| Et$_2$O | Diethyl ether |
| Fmoc | 9-Fluorenylmethoxycarbonyl |
| HOBT | Hydroxybenzotriazole |
| i-Pr | Isopropyl |
| NMM | N-Methylmorpholine |
| OSu | N-Oxysuccinimide |
| Pmc | 2,2,5,7,8-Pentamethylchroman-6-sulfonyl |
| PTSA | p-Toluenesulfonic acid |
| RT | room temperature |
| TFA | Trifluoroacetic acid |

Amino acid abbreviations are defined below:

| Ala | Alanine |
|---|---|
| β-Ala | beta-Alanine |
| Arg | Arginine |
| Asp | Aspartic Acid |
| Cha | Cyclohexylalanine |
| ρ-F-Phe | 4-Fluorophenylalanine |
| Glu | Glutamic Acid |
| Gly | Glycine |
| hArg | Homoarginine (homoArg) |
| His | Histidine |
| Ile | Isoleucine |
| Leu | Leucine |
| Lys | Lysine |
| Or | Ornithine |
| Phe | Phenylalanine |
| Sar | Sarcosine |
| Ser | Serine |
| Thr | Threonine |
| Tyr | Tyrosine |

Methyl 2-[1(S)-t-butoxycarbonylamino-2-(4-fluorophenyl)ethyl]oxazole-4-carboxylate (AA2)

To a solution of Boc-p-F-Phe-OH (0.018 mol), DCM (200 mL), H-Ser-OMe (0.018 mol), HOBT (10 mg), and EDC.HCl (0.036 mol) at 5° C. was added NMM (0.036 mol). The reaction was stirred for 3.5 h, diluted with sat'd NH$_4$Cl (30 mL). The layers were separated, and the organic layer was washed with sat'd NAHCO$_3$ (30 mL), dried (Na$_2$SO$_4$), and evaporated to give a white powder (5.9 g). The powder was dissolved in DME (100 mL), treated with (methoxycarbonylsulfamoyl) triethylammonium hydroxide (0.015 mol), and heated at reflux for 1 h. The reaction was cooled to RT, diluted with EtOAc (150 mL) and sat'd NaHCO$_3$ (30 mL), and the layers separated. The organic layer was dried (Na$_2$SO$_4$) and evaporated to give a white solid (4.8 g). The solid was dissolved in benzene (140 mL), treated with Cu(OAc)$_2$ (0.014 mol), CuBr (0.014 mol), and t-butyl peroxybenzoate (0.020 mol), and heated at reflux for 5 h. The reaction was cooled, diluted with EtOAc (50 mL) and sat'd NaHCO$_3$ (10 mL), and filtered. The layers of the filtrate were separated, and the organic layer dried and evaporated to a brown oil. The oil was purified over silica gel (2% MeOH/DCM) to give AA2 as a gold solid (1.75 g): $^1$H NMR (CDCl$_3$) δ8.12 (s, 1H), 7.6 (m, 1H), 6.9 (m, 4H), 5.2 (m, 1H), 3.91 (s, 3H), 3.2 (m, 2H), 1.40 (s, 9H); FAB-MS m/e 365 (MH+).

The following examples describe the invention in greater detail and are intended to illustrate the invention but not to limit it.

Example 1

2-[1(S)-Sarcosineamido-2-(4-fluorophenyl)ethyl] oxazole-4-carboxycyclohexylalanyl-arginine benzylamide (1)

Intermediate AA2 (4.1 mmol) was dissolved in DCM (10 mL) and TFA (12 mL) and stirred for 1 h. The solution was concentrated to give a brown oil, and the oil triturated with hexane (50 mL). The oil was dissolved in DCM (60 mL), treated with Boc-Sar-OSu (4.1 mmol) and NMM (12.3 mmol), and stirred for 24 h. The reaction mixture was diluted with sat'd $NH_4Cl$ (15 mL) and the layers separated. The organic layer was washed with sat'd $NaHCO_3$ (20 mL), dried $Na_2SO_4$), evaporated, and purified by silica gel chromatography (2%MeOH/DCM) to give a brown oil (AA3, 1.0 g). AA3 (2.1 mmol) was dissolved in THF (10 mL), cooled to 5° C., treated with aq. LiOH (4 mmol/20 mL water), and stirred for 2 h. The reaction was acidified with citric acid (0.5 g) and extracted with $CHCl_3$ (2×70 mL). The organic materials were dried ($Na_2SO_4$) and evaporated to give a gold foam (0.85 g). The foam (2.0 mmol) was dissolved in DCM (60 mL) and treated with H-CHa-OMe.HCl (2.0 mmol), HOBT (10 mg), EDC.HCl (3.0 mmol), and NMM (4.0 mmol). This mixture was stirred for 2 h, diluted with sat'd $NH_4Cl$ (20 mL), and the layers separated. The organic layer was dried, evaporated, and purified by silica gel chromatography (3% MeOH/DCM) to afford a gold oil (AA4, 1.0 g; FAB-MS m/e 589, MH+). AA4 (1.7 mmol) was dissolved in THF (10 mL), cooled to 5° C., treated with aq. LiOH (3.4 mmol/20 mL water), and stirred for 2 h. The reaction was acidified with citric acid (0.5 g) and extracted with $CHCl_3$ (2×70 mL). The organic materials were dried ($Na_2SO_4$) and evaporated to give a gold oil (0.71 g). The oil (1.2 mmol) was dissolved in DCM (60 mL) and treated with H-Arg(Pmc)-$NHCH_2Ph$ (1.2 mmol), HOBT (10 mg), EDC.HCl (2.4 mmol), and NMM (1.2 mmol). This mixture was stirred for 2 h, diluted with sat'd $NH_4Cl$ (20 mL), and the layers separated. The organic layer was dried ($Na_2SO_4$), evaporated, and purified by silica gel chromatography (7% EtOH/DCM) to afford a clear glass (0.90 g). The glass was dissolved in DCM (5 mL) and anisole (0.5 mL), treated with TFA (10 mL), and stirred for 2.5 h. The solution was evaporated, and the resultant green oil triturated with $Et_2O$ (4×30 mL), dried $Na_2SO_4$, and isolated as a white powder (0.90 g): mp 127–130° C.; FAB-MS m/e 720 ($MH^+$); $[\alpha]^{24}D$ −21.8° (c 0.28, MeOH). Anal. calcd. for $C_{37}H_{50}N_9O_5F.2.0$ TFA (947.91): C, 51.95; H, 5.53; N, 13.30. Found: C, 51.53; H, 5.78; N, 13.05.

Example 2

2-[1(S)-β-Alanineamido-2-(4-fluorophenyl)ethyl] oxazole-4-carboxycyclohexylalanyl-arginine benzylamide (2)

Compound 2 was prepared using the method described in example 1. Intermediate AA2 (2.2 mmol) was deprotected with TFA and then reacted with H-β-Ala-OSu (2.2 mmol) as described. Compound 2 was isolated as a white powder (0.21 g); mp 108–112° C.; FAB-MS m/e 720 (MH+). Anal. calcd. for $C_{37}H_{50}N_9O_5F.2.0$ TFA.0.5 $H_2O$ (956.93): C, 51.46; H, 5.58; N, 13.17; KF, 0.91. Found: C, 51.41; H, 5.95; N, 13.20; KF, 0.88.

Ethyl 2-[1(S)-t-butoxycarbonylamino-2-(4-fluorophenyl)ethyl]thiazole-4-carboxylate (AB2)

To a solution of AB1 (14.9 mmol) in dioxane (60 mL) was added Lawesson's reagent (8.9 mmol). This mixture was stirred for 3 h, filtered, and the filtrate evaporated and purified by silica gel chromatography (2% MeOH/DCM) to afford the thioamide (3.9 g). The thioamide (13.1 mmol) was dissolved in DME (80 mL), treated with $NaHCO_3$ (0.10 mol) and ethyl bromopyruvate (39.3 mmol), and stirred for 20 min. The mixture was cooled to 5° C., treated with a solution of TFAA (52.4 mmol), pyridine (0.10 mol), and DME (10 mL), and the ice bath removed. This mixture was stirred for 17 h, filtered, concentrated, diluted with DCM, and washed with water. The organic layer was dried ($Na_2SO_4$) and purified by silica gel chromatography (1.5% MeOH/DCM) to afford AB2 as a white foam (4.6 g); $^1$H NMR ($CDCl_3$) δ8.08 (s, 1H), 7.1 (m, 2H), 6.9 (m, 2H), 5.3 (m, 2H), 4.4 (q, 2H), 3.2 (m, 2H), 1.5 (t, 3H), 1.40 (s, 9H); FAB-MS m/e 395 ($MH^+$).

Example 3

2-[1(S)-Sarcosineamido-2-(4-fluorophenyl)ethyl] thiazole-4-carboxy-cyclohexylalanyl-arginine phenethylamide (3)

Compound 3 was prepared by the method described for compound 1. Intermediate AB1 (1.2 mmol) was dissolved in DCM (10 mL) and TFA (12 mL) and the resultant solution was stirred for 1 h. The solution was then concentrated to give a brown oil, and the oil triturated with hexane (50 mL). The oil was dissolved in DCM (60 mL), treated with Boc-Sar-OSu (1 mmol) and NMM (3 mmol), and stirred for 24 h. The reaction was diluted with sat'd $NH_4Cl$ (15 mL) and the layers separated. The organic layer was washed with sat'd $NaHCO_3$ (20 mL), dried ($Na_2SO_4$), evaporated, and purified by silica gel chromatography (2%MeOH/DCM) to give an oil. The oil was dissolved in THF (10 mL), cooled to 5° C., treated with aq. LiOH (1 mmol/6 mL water), and stirred for 2 h. The reaction was acidified with citric acid (0.2 g) and extracted with $CHCl_3$ (2×70 mL). The organic materials were dried ($Na_2SO_4$) and evaporated to give a foam. The foam (0.5 mmol) was dissolved in DCM (60 mL) and treated with H-Cha-OMe.HCl (0.5 mmol), HOBT (3 mg), EDC.HCl (1 mmol), and NMM (1.5 mmol). This mixture was stirred for 2 h, diluted with sat'd $NH_4Cl$ (20 mL), and the layers separated. The organic layer was dried ($Na_2SO_4$), evaporated, and purified by silica gel chromatography (3% MeOH/DCM) to afford a clear oil. The oil was dissolved in THF (5 mL), cooled to 5° C., treated with aq. LiOH (0.2 mmol/4 mL water), and stirred for 2 h. The reaction was acidified with citric acid (0.5 g) and extracted with $CHCl_3$ (2×50 mL). The organics were dried ($Na_2SO_4$) and evaporated to give a gold oil (0.71 g). The oil (1.2 mmol) was dissolved in DCM (60 mL) and treated with H-Arg(Pmc-$NHCH_{CH2}Ph$ (1.2 mmol), HOBT (10 mg), EDC.HCl (2.4 mmol), and NMM (1.2 mmol). This mixture was stirred for 2 h, diluted with sat'd $NH_4Cl$ (20 mL), and the layers separated. The organic layer was dried, evaporated, and purified by silica gel chromatography (7% EtOH/DCM) to afford a clear glass (0.3 g). The glass was dissolved in DCM (5 mL) and anisole (0.5 mL), treated with TFA (10 mL), and stirred for 2.5 h. The solution was evaporated, and the resultant brown oil triturated with Et$_2$O (4×30 mL), dried and isolated as a beige powder (0.093 g): $^1$H NMR (DMSO-d$_6$) δ9.2 (m, 2H), 8.4 (d, 1H), 8.33 (s, 1H), 8.2 (m, 1H), 8.1 (m, 1H), 7.6 (m, 1H), 6.9–7.4 (m, 9H), 5.4 (m, 1H), 4.6 (m, 1H), 4.2 (m, 1H), 3.6 (q, 2H), 3.0–3.5 (m, 6H), 2.7 (m, 2H), 2.5 (m, 2H), 2.39 (s, 3H), 1.3–1.9 (m, 10H), 0.8–1.3 (m, 10H); FAB-MS m/e 750 (MH$^+$).

Example 4

2-[1(S)-Sarcosineamido-2-(4-fluorophenyl)ethyl]thiazole-4-carboxy-cyclohexylalanyl-homoarginyl-phenylalanineamide (4)

Compound 4 was prepared by the method described in example 3 from AB2 (1.0 mmol) and Boc-Sar-OSu (1.0 mmol), and isolated as a tan powder (0.021 g): $^1$H NMR (DMSO-d$_6$) δ8.38 (s, 1H), 8.0 (d, 1H), 7.9 (d, 1H), 7.5 (m, 1H), 7.0–7.4 (m, 9H), 5.4 (m, 1H), 4.6 (m, 1H), 4.4 (m, 1H), 4.2 (m, 1H), 3.7 (q, 2H), 3.4 (m, 4H), 3.1 (m, 4H), 2.8 (m, 2H), 2.47 (s, 3H), 1.7 (m, 1H), 1.3–1.8 (m, 8H), 0.8–1.4 (m, 16H); FAB-MS m/e 807 (MH$^+$).

Example 5

2-[1(S)-Isoleucineamido-2-(4-fluorophenyl)ethyl]thiazole-4-carboxy-cyclohexylalanyl-arginyl-phenylalanineamide (5)

Compound 5 was prepared aby the method described in example 3 from AB2 (1.3 mmol) and Boc-Ile-OH (1.3 mmol), and isolated as a pale yellow powder (0.079 g): $^1$H NMR (DMSO-d$_6$) δ9.2 (m, 1H), 8.8 (m, 1H), 8.72 (s, 1H), 7.7–8.1 (m, 7H), 7.6 (m, 1H), 6.8–7.5 (m, 9H), 5.4 (m, 1H), 4.6 (m, 1H), 4.4 (m, 1H), 4.3 (m, 1H), 3.7 (m, 2H), 3.6 (m, 1H), 3.4 (m, 2H), 2.7–3.2 (m, 6H), 1.8 (m, 2H), 1.0–1.7 (m, 18H), 0.9 (d, 3H), 0.8 (t, 3H); FAB-MS m/e 835 (MH$^+$).

Example 6

2-[1(S)-Sarcosineamido-2-(4-fluorophenyl)ethyl]thiazole-4-carboxy-lysyl-arginine phenethylamide (6)

Compound 6 was prepared by the method described in example 3 from AB2 (1.4 mmol) and Boc-Sar-OSu (1.4 mmol), and isolated as a tan powder (0.099 g): FAB-MS m/e 725 (MH$^+$).

Methyl 2-[1(S)-t-butoxycarbonylamino-2-(4-fluorophenyl)ethyl]-5-methyloxazole-4-carboxylate (AC2)

Dipeptide AC1 (12.6 mmol), prepared by the method described for the preparation of Boc-p-F-Phe-Ser-OMe in example AA2, was dissolved in DCM (125 mL) and water (0.2 mL) and treated with 1,1,1-tris(acetyloxy)-1,1-dihydro-1,2-benzodioxol-3-(1H)-one (Dess-Martin reagent; 15.1 mmol). The reaction was stirred for 30 min, diluted with DCM (100 mL), and washed with sat'd NaHCO$_3$ (2×40 mL), dried, and evaporated. The residue was purified by silica gel chromatography (30% EtOAc/hexane) to give a ketone. A solution of DCM (70 mL), PPh$_3$ (8.3 mmol), and TEA (16.5 mmol) was treated with the ketone (8.3 mmol) and stirred for 5 min. The mixture was washed with aq. Na$_2$S$_2$O$_3$ and sat'd NaHCO$_3$, and the organic layer dried, evaporated, and purified by silica gel chromatography (25% EtOAc/hexane) to give AC2 as a white foam (2.5 g): $^1$H NMR (CDCl$_3$) δ7.1 (m, 2H), 6.9 (m, 2H), 5.1 (m, 2H), 3.92 (s, 3H), 3.2 (m, 2H), 2.60 (s, 3H), 1.40 (s, 9H); FAB-MS m/e 379 (MH$^+$).

Example 7

2-[1(S)-Sarcosineamido-2-(4-fluorophenyl)ethyl]-5-methyloxazole-4-carboxy-cyclohexylalanyl-arginine benzylamide (7)

Compound 7 was prepared by the method described for the preparation of compound 1. Intermediate AC1 (1.3 mmol) was dissolved in DCM (10 mL) and TFA (12 mL) and the solution was stirred for 1 h. The solution was concentrated to give a tan oil, and the oil triturated with hexane (50 mL). The oil was dissolved in DCM (60 mL), treated with Boc-Sar-OSu (1.3 mmol) and NMM (4 mmol), and stirred for 24 h. The reaction was diluted with sat'd NH$_4$Cl (15 mL) and the layers separated. The organic layer was washed with sat'd NaHCO$_3$ (20 mL), dried (Na$_2$SO$_4$), evaporated, and purified by silica gel chromatography (2%MeOH/DCM) to give an oil. The oil was dissolved in THF (10 mL), cooled to 5° C., treated with aq. LiOH (1 mmol/6 mL water), and the mixture stirred for 2 h. The reaction mixture was acidified with citric acid (0.2 g) and extracted with CHCl$_3$ (2×70 mL). The organic materials were dried (Na$_2$SO$_4$) and evaporated to give a foam. The foam (0.6 mmol) was dissolved in DCM (60 mL) and the solution was treated with H-Cha-OMe.HCl (0.6 mmol), HOBT (3 mg), EDC.HCl (1 mmol), and NMM (1.5 mmol). This mixture was stirred for 2 h, diluted with sat'd NH$_4$Cl (15 mL), and the layers separated. The organic layer was dried (Na$_2$SO$_4$), evaporated, and the residue was purified by silica gel chromatography (3% MeOH/DCM) to afford a tan oil. The oil was dissolved in THF (5 mL), cooled to 5° C., treated with aq. LiOH (0.2 mmol/4 mL water), and the mixture was stirred for 2 h. The reaction mixture as then was acidified with citric acid (0.5 g) and extracted with CHCl$_3$ (2×50 mL). The organic materials were dried (Na$_2$SO$_4$) and evaporated to give a glass (0.71 g). The glass (1.2 mmol) was dissolved in DCM (60 mL) and the solution was treated with H-Arg (Pmc)-NHBn (1.2 mmol), HOBT (5 mg), EDC.HCl (2.4 mmol), and NMM (1.2 mmol). This mixture was stirred for 2 h, diluted with sat'd NH$_4$Cl (20 mL), and the layers separated. The organic layer was dried (Na$_2$SO$_4$), evaporated, and the residue was purified by silica gel chromatography (7% EtOH/DCM) to afford a clear glass (0.3 g). The glass was dissolved in DCM (5 mL) and anisole (0.5 mL), the resultant solution was treated with TFA (10 mL), and stirred for 2.5 h. The solution was evaporated, and the resultant glass triturated with Et$_2$O (4×25 mL), dried (Na$_2$SO$_4$), and isolated as a white powder (0.10 g): mp 117–121° C.; FAB-MS m/e 734 (MH$^+$). Anal. calcd. for C$_{38}$H$_{52}$N$_9$O$_5$F.2.0 TFA.0.5 H$_2$O (970.94); C, 51.96; H, 5.71; N, 12.98; KF, 0.94. Found: C, 51.88; H, 5.89; N, 12.60; KF, 1.0.

Example 8

2-[1(S)-N(tau)-Benzyl-histidineamido-2-(4-fluorophenyl)ethyl]-5-methyloxazole-4-carboxy-cyclohexylalanyl-arginine benzylamide (8)

Compound 8 was prepared by the method described for the preparation of compound 7 from AC2 (1.1 mmol) and Boc-His(Bn)-OH (1.1 mmol), and isolated as a white powder (0.083 g): mp 101–106° C.; FAB-MS m/e 890 (MH$^+$). Anal. calcd. for $C_{48}H_{60}N_{11}O_5F$.2.6 TFA.0.8 anisole.1.0 H$_2$O (1294.5): C, 54.61; H, 5.53; N, 11.90; KF, 1.39. Found: c, 54.23; H, 5.44; N, 11.96; KF, 1.75.

Example 9

2-[1(S)-Acetamido-2-(4-fluorophenylethyl]-5-methyloxazole-4-carboxy-cyclohexylalanyl-arginine benzylamide (9)

Compound 9 was prepared by the method described for the preparation of compound 7 from AC2 (1.2 mmol) and acetyl chloride (1.2 mmol), and isolated as a white powder (0.10 g): mp 111–116° C.,; FAB-MS m/e 705 (MH$^+$). Anal. calcd. for $C_{37}H_{49}N_8O_5F$.1.0 TFA.1.0 anisole.1.0 H$_2$O (901.78): C, 57.54; H, 6.35; N, 12.43; KF, 2.0. Found: C, 57.71; H, 6.27; N, 12.49; KF, 2.32.

Example 10

2-[1(S)-N,N-Dimethyl-2-(4-fluorophenylethyl]-5-methyloxazole-4-carboxy-cyclohexylalanyl-arginine benzylamide (10)

Compound 10 was prepared by the method described for the peparation of compound 7, was synthesized via methyl 2-[1(S)-N,N-dimethyl-2-(4-fluorophenyl)ethyl]-5-methyloxazole-4-carboxylate as follows. Intermediate AC2 (1.0 mmol) was deprotected of the Boc group with TFA as described. The primary amine TFA salt was partitioned between DCM (50 mL) and sat'd NaHCO$_3$ (15 mL), and the layers separated. The organic layer was dried (Na$_2$SO$_4$) and evaporated to a glass. The glass was dissolved in DCE (10 mL) and 37% formaldehyde (0.23 mL) at RT and then treated with sodium triacetoxyborohydride (4.0 mmol). The mixture was stirred for 18 h, diluted with DCM (50 mL), and washed with sat'd NAHCO$_3$ (10 mL). The organic layer was dried (Na$_2$SO$_4$), evaporated, and the resultant foam purified by silica gel chromatography (1.5% MeOH/DCM) to afford methyl 2-[1(S)-N,N-dimethyl-2-(4-fluorophenyl)ethyl]-5-methyloxazole-4-carboxylate as a glass (0.24 g). This glass was used to prepare 10 aby the method described in example 7. Compound 10 was isolated as a tan powder (0.088 g): mp 115° C.; FAB-MS m/e 691 (MH$^+$). Anal. calcd. for $C_{37}H_{51}N_8O_4F$.2.0 TFA.2.1 H$_2$O (956.75); C, 51.47; H, 6.03; N, 11.71; KF, 3.95. Found: C, 51.24; H, 6.28; N, 12.09; KF, 4.23.

---

---

We claim:

1. A method of treating platelet-mediated thrombotic disorders comprising administering to a patient afflicted with such disorder an effective amount of the compound of the general formula (I)

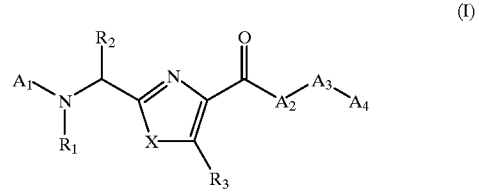

(I)

wherein A$_1$ is an amino acid residue selected from the Sar, Gly, His, His(CH$_2$Ph), Ile, Ser, Thr, β-Ala, Ala, a C$_2$–C$_6$-acyl group and a C$_1$–C$_8$-alkyl group;

wherein A$_2$ is an alkyl amino acid residue selected from Cha, Leu, Ile, Asp, and Glu or an amino alkyl amino acid residue selected from Lys, His, Orn, homoArg and Arg;

wherein $A_3$ is an amino alkyl amino acid residue selected from Lys, His, Orn, Arg and homoArg;

wherein $A_4$ is an arylalkyl residue selected from Phe and Tyr or an aralkylamino group;

wherein $R_1$ is selected from H or alkyl;

wherein $R_2$ is an aryl, substituted aryl, heteroaryl, substituted heteroraryl aralkyl or substituted aralkyl;

wherein $R_3$ is H or alkyl;

wherein X is selected from S, O, or $NR_4$, wherein $R_4$ is selected from H or alkyl;

and the pharmaceutically acceptable salts thereof to treat such disorder.

2. The method of claim 1, wherein the amount is 0.03 mg to 100 mg/kg/day.

* * * * *